(12) United States Patent
Lin

(10) Patent No.: US 6,863,528 B2
(45) Date of Patent: Mar. 8, 2005

(54) ORTHODONTIC PIN

(76) Inventor: Fu Yi Lin, No. 34, Alley 43, Lane 123, Sec. 6, Minchiuan E. Rd., Neihu Chiu, Taipei (TW)

( * ) Notice: Subject to any disclaimer, the term of this patent is extended or adjusted under 35 U.S.C. 154(b) by 182 days.

(21) Appl. No.: 10/263,095

(22) Filed: Oct. 3, 2002

(65) Prior Publication Data

US 2004/0067464 A1 Apr. 8, 2004

(51) Int. Cl.[7] .................................................. A61D 5/00
(52) U.S. Cl. ......................................... 433/18; 433/173
(58) Field of Search .......................... 433/18, 173, 174; 606/73

(56) References Cited

U.S. PATENT DOCUMENTS 5,961,329 A * 10/1999 Stucki-McCormick ...... 433/173

6,726,475 B2 * 4/2004 Lin ............................ 433/18

* cited by examiner

Primary Examiner—Cary E. O'Connor
Assistant Examiner—Candice C. Stokes

(57) ABSTRACT

An orthodontic pin includes a pin body and a fastening member screwed into the pin body. An elastic element is connected at an end to the orthodontic pin by extending the fastening member through a ring provided at the end of the elastic element before screwing it into the pin body. When the elastic element becomes loose due to any change in the position of a tooth being corrected, it can be determined the elastic element needs replacement. Since the fastening member can be easily loosened from the pin body of the orthodontic pin, the elastic element can be conveniently removed from the pin body to facilitate quick replacement of the elastic element.

6 Claims, 5 Drawing Sheets

ORTHODONTIC PIN

BACKGROUND OF THE INVENTION

The present invention relates to an orthodontic pin, and more particularly to an orthodontic pin including an easily detachable connected pin body and fastening member that enables quick replacement of an elastic element connecting the orthodontic pin to orthodontic hook and brackets when the elastic element becomes loose due to any change in the position of a corrected tooth.

People who have the problems of snaggleteeth or malocclusion, particularly at the upper and lower incisors, would usually seek orthodontia treatment at hospitals or clinics for the purpose of corrective therapy or aesthetic surgery. Most dentists would generally recommend to the patients to correct malaligned or maloccludent teeth as soon as possible, so as to enable shortened time needed in orthodontia and obtain a highly stable correcting effect. In a currently most common practice of orthodontia, orthodontic pins are used with corrective wires, orthodontic brackets, and pull hooks to perform traction of teeth on a long term basis.

When using the orthodontic pin to correct malaligned or maloccludent teeth, the orthodontic pin and the crown of a posterior tooth are used as points of application to produce a traction force, so that an anterior tooth would turn about a point below a center of resistance indicated by the cross 23 in FIG. 3, which is normally the center of resistance for the six most front teeth, to incline inward only. Therefore, before the orthodontia procedure, an orthodontist has to find out the center of resistance 23 of the teeth to be corrected, incise the gum below the line A—A, drill a hole in the bone behind the gum, implant an orthodontic pin 1, such as the one shown in FIG. 1, into the hole in the bone via the incised gum, and then suture the incision on the gum.

Sutures are removed about one week later. The incision is examined for exact healing thereof after another one or two weeks. Thereafter, orthodontic brackets 2 are attached to outer surfaces of the teeth to be corrected, a molding wire 21 is tightly pulled and fixed in place, and a corrective wire 3 is used to connect a pull hook 22 pre-attached to the molding wire 21 to a groove 11 provided around a head portion of the orthodontic pin 1 (see FIG. 2), so as to pull the hook 22 toward the orthodontia pin 1. The corrective wire 3 is adjusted to a length corresponding to the required correction amount of the tooth.

As shown in FIG. 3, the corrective wire 3 extended between the orthodontic pin 1 and the pull hook 22 is used to pull the tooth to be corrected in a desired direction. In the event there is still another tooth to be corrected, another hole is drilled to implant a further orthodontic pin 1 into the bone behind the gum, and the same steps as described above are repeated to fix the corrective wire 3 between the groove 11 of the further orthodontic pin 1 and a corresponding pull hook 22 for the purpose of orthodontia.

In the above conventional orthodontia, the corrective wire 3 is connected to the orthodontic pin 1 and the pull hook 22 on the molding wire 21 by separately winding two ends of the corrective wire 3 around the groove 11 and the pull hook 22. When doing so, it is necessary to pull the molding wire 21 tight before the corrective wire 3 can be wound around the groove 11 of the orthodontic pin 1 and the pull hook 22. Moreover, tools for tightening the molding wire 21 and winding the corrective wire 3 are very small in size. Thus, it takes a prolonged time and great cares to perform the orthodontia, which becomes a laborious task for both the orthodontist and the patient.

When a period of time has elapsed after the orthodontia has been conducted, the teeth being corrected must be examined for their current conditions. The gradual correction of teeth in position results in gradual loosening of the corrective wire 3. That is, the corrective wire 3 is no longer tight enough to provide sufficient pull. At this point, the corrective wire 3 must be loosened and wound again. The time required to loosen and wind the corrective wire 3 again is even longer than the time needed in the first winding. Such adjustment of the corrective wire 3 does not upgrade the quality of medical treatment of the conventional orthodontia, but brings further discomfort to the orthodontist and the patent.

In the orthodontia using the conventional orthodontic pin 1, the molding wire 21 must be repeatedly tightened and the corrective wire 3 must be repeatedly wound. Therefore, increased treatment cost is required and the patent has to endure pain and discomfort in the course of tooth treatment.

In view of today's largely upgraded living quality, it is absolutely necessary to develop an improved orthodontic pin to minimize the patient's pain and discomfort in the process of correcting the malaligned or maloccludent teeth, either for necessary therapy or simply for aesthetic surgery.

It is therefore tried by the inventor to develop an orthodontic pin that includes a pin body and a fastening member detachably connected to the pin body, and is used with an elastic element to correct snaggletooth and malocclusion, so that the elastic element can be easily and quickly detachably connected to the orthodontic pin to facilitate quick replacement thereof when a condition of the corrected tooth causes change of tensional force provided by the elastic element.

SUMMARY OF THE INVENTION

A primary object of the present invention is to provide an orthodontic pin that includes a pin body and a fastening member detachably connected to the pin body, and is used with an elastic element to correct snaggletooth and malocclusion, so that the elastic element can be easily and quickly detachably connected to the orthodontic pin to facilitate quick replacement thereof when a condition of the corrected tooth causes change of tensional force provided by the elastic element.

To achieve the above and other objects, the orthodontic pin of the present invention mainly includes a pin body and a fastening member screwed into a top of the pin body. An elastic element is connected at an end to a joint of the pin body and the fastening member that have been screwed together, and at another end to a pull hook provided on a molding wire that is used to tighten an orthodontic bracket to the surface of a tooth to be corrected. Whereby when the tooth is gradually corrected to a desired position and such change of position of the tooth causes loosening of the elastic element between the orthodontic pin and the pull hook, it can be easily judged the elastic element needs replacement. Since the fastening member can be quickly loosened from and screwed into the pin body again, the old elastic element could be quickly removed from the orthodontic pin and the pull hook, and a new spring providing suitable tension could be quickly connected to and between the orthodontic pin and the pull hook to replace the old one. That is, the orthodontic pin of the present invention enables simplified and fast replacement of a suitable elastic member for pulling the pull hook and accordingly the molding wire corresponding to an actual corrective condition of the corrected tooth.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION OF THE PREFERRED EMBODIMENTS

Figure 1:
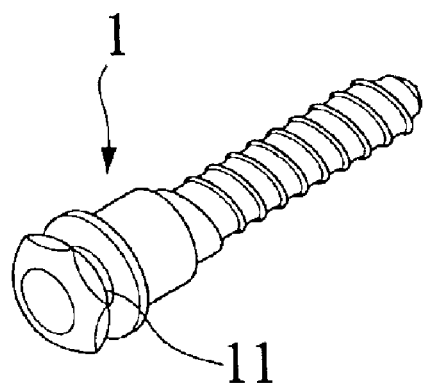
FIG. 1 is a perspective view of a conventional orthodontic pin.
Figure 2:
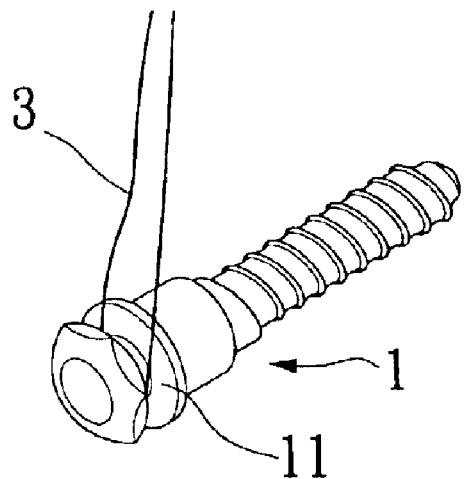
FIG. 2 shows the use of the conventional orthodontic pin of FIG. 1 with a corrective wire.
Figure 3:
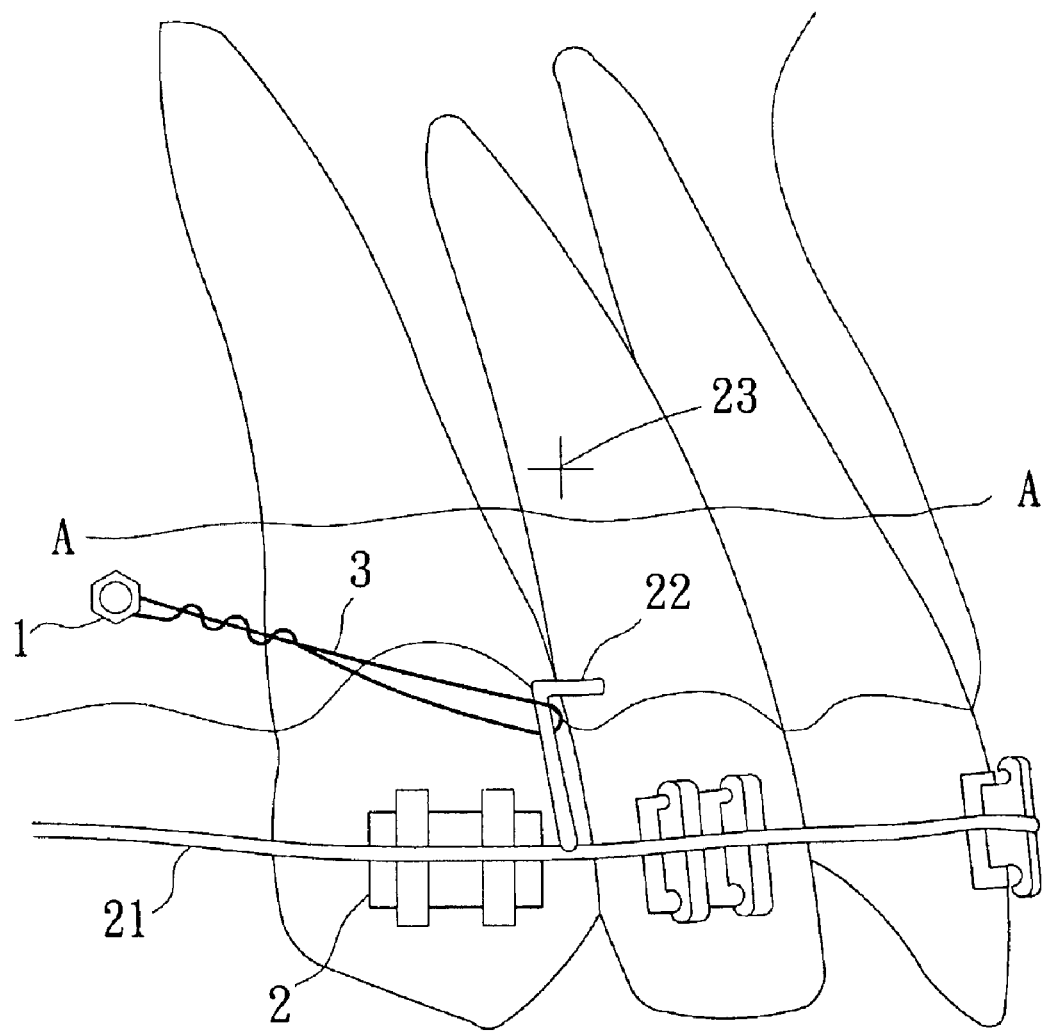
FIG. 3 shows the manner of using the conventional orthodontic pin of FIG. 1 with other orthodontic means to correct malaligned or maloccludent teeth.
Figure 4:
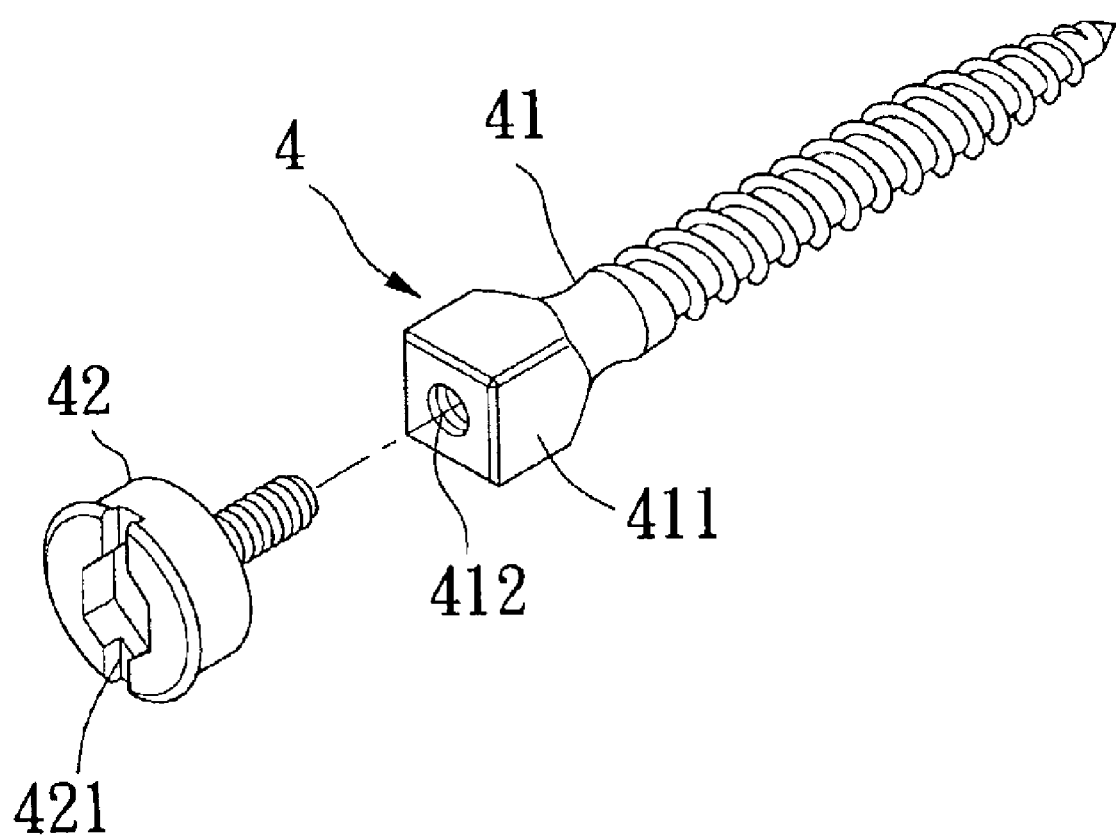
FIG. 4 is an exploded perspective view of an orthodontic pin according to the present invention.
Figure 5:
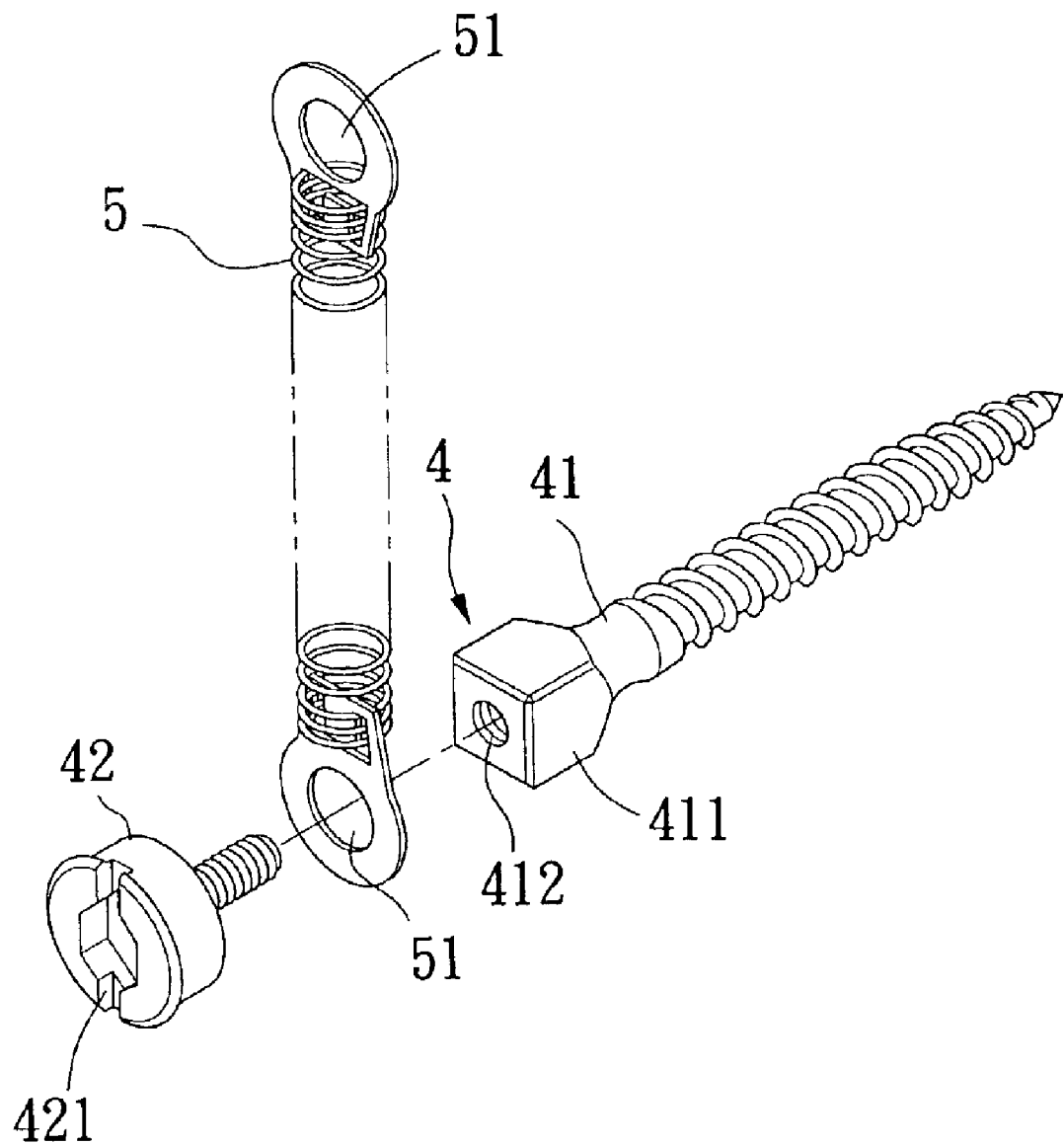
FIG. 5 shows the use of the orthodontic pin of FIG. 4 with a tension spring.

Please refer to FIG. 4 that is an exploded perspective view of an orthodontic pin 4 according to the present invention, and to FIG. 5 that shows the orthodontic pin 4 being used with an elastic element 5 in an orthodontia.

As shown, the orthodontic pin 4 mainly includes a pin body 41 having a top formed into a receiving head 411, in which an internally threaded hole 412 is provided; and a fastening member 42 in the form of a slotted head screw having a straight slot 421 provided on a top for tightening with a slotted screwdriver. Alternatively, the fastening member 42 may be a Philips headed screw having a cross recess for tightening with a Philips screwdriver, or a hexagonal head screw for tightening with a hexagonal wrench. The fastening member 42 is adapted to screw into the threaded hole 412 on the receiving head 411 of the pin body 41.

The elastic element 5 may be a tension spring 5 having two ends separately connected to two rings or to a ring and a hook, so that the fastening member 42 may be extended through a hole 51 on the ring or the hook before being screwed into the threaded hole 412 on the pin body 41.

When using the orthodontic pin 4 in an orthodontia, the orthodontist also has to employ his professional skill and experience to locate the center of resistance of the teeth to be corrected, in order to implant orthodontic pins 4 into appropriate positions. Since this procedure is a common practice and skill in orthodontia, it is not repeatedly described herein. However, some features and advantages of the orthodontic pin 4 of the present invention will become apparent from the following description of the use thereof.

Figure 6:
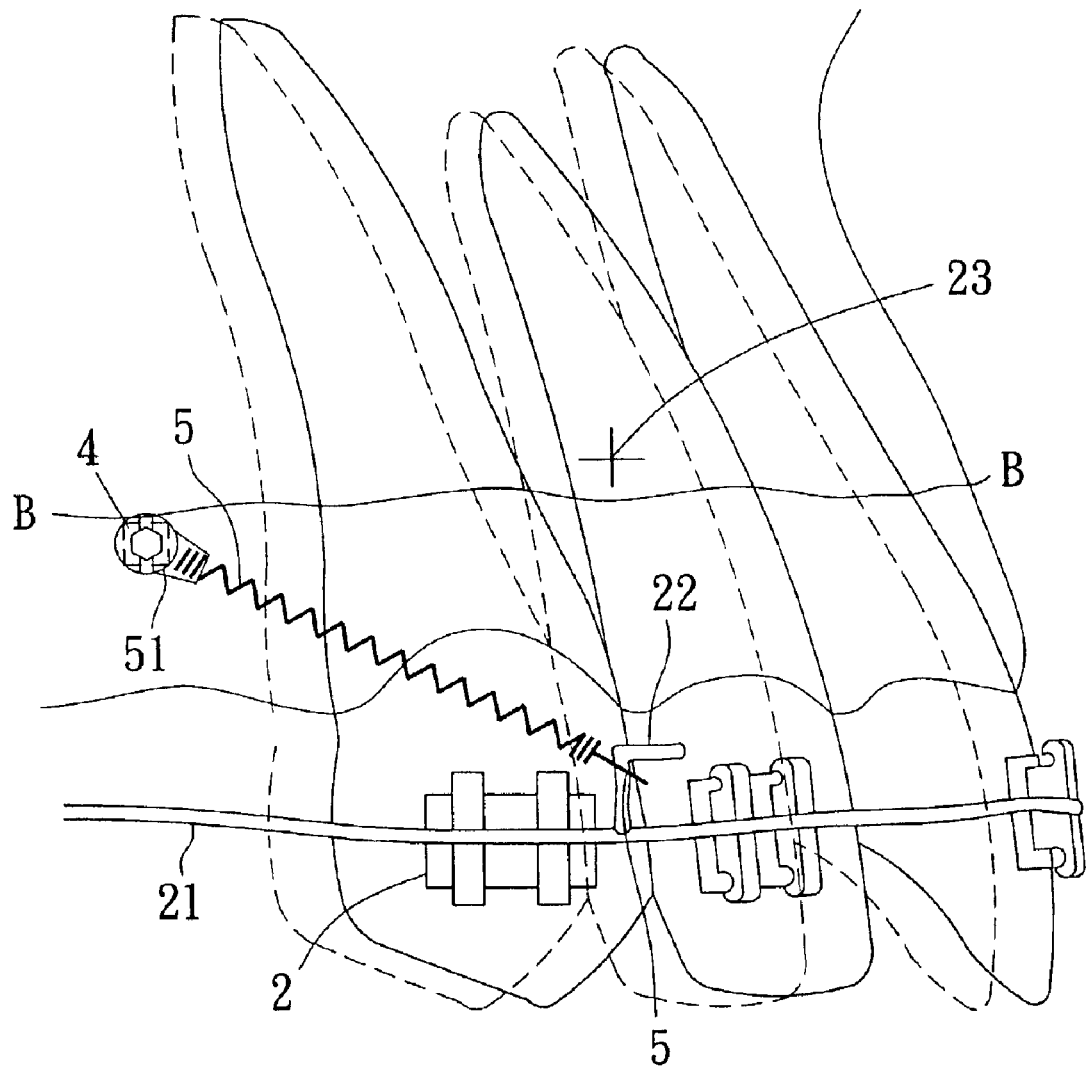
FIG. 6 shows the manner of using the orthodontic pin of FIG. 4 with other orthodontic means to correct malaligned or maloccludent teeth.

Please refer to FIG. 6 that shows an example of using the orthodontic pins 4 of the present invention in an orthodontia to correct malaligned or maloccludent teeth. As shown, the pin body 41 of each orthodontic pin 4 is screwed into the bone via an incision at a position closely below line B—B that is located below the center of resistance 23 indicated in FIG. 6. After the incision is sutured, and sutures are removed after a period of time, and the incision is fully healed, orthodontic brackets 2 are separately attached to outer surfaces of the teeth to be corrected and fixed in place with a molding wire 21. Meanwhile, the fastening member 42 is extended through the hole 51 at one end of the tension spring 5 and into the threaded hole 412 on the receiving head 411 of the pin body 41, and then pulled, so that the hole 51 at the other end of the tension spring 5 can be hooked to a corresponding pull hook 22 provided on the molding wire 21 at a predetermined position, so that a corresponding tooth can be corrected to a position indicated by the broken line in FIG. 6 through a tight traction by a restoring force of the tension spring 5.

When the orthodontist finds in regular follow-up during the course of tooth corrective therapy the tension spring 5 has become loose due to a prolonged tension thereof or a shift of the corrected tooth in position, the old and loose tension spring 5 can be removed by first releasing the ring with the hole 51 at one end of the spring 5 from the pull hook 22 and then loosening the fastening member 42 from the pin body 41 by aligning a suitable slotted screwdriver with the straight slot 421 on the fastening member 42. A new tension spring 5 may be then used to replace the old one by separately connecting the rings 51 at two ends thereof to the pin body 41 and the pull hook 22 on the molding wire 21, and the fastening member 42 to the pin body 41 is tightened again to complete the replacement of the tension spring 5.

The orthodontic pin 4 of the present invention is superior to the conventional orthodontic pin 1 because the quickly detachably connected pin body 41 and fastening member 42 enables easy and quick mounting and replacement of the tension spring 5 when the tension spring 5 is found to be loose due to shifting of the corrected tooth in position.

The present invention has been described with a preferred embodiment thereof and it is understood that many changes and modifications in the described embodiment can be carried out without departing from the scope and the spirit of the invention as defined by the appended claims.

What is claimed is:

1. An orthodontic pin arrangement, comprising:
    an elastic element having a ring disposed at an end thereof; and
    an orthodontic pin, including:
        a pin body having a top formed into a receiving head, in which an internally threaded hole is provided; and
        a fastening member adapted to extend through the ring of said elastic element and then removably screwed into the threaded hole in said receiving head so as to removably fasten said elastic element to said orthodontic pin;
        wherein when said elastic element needs to be replaced, said fastening member is unscrewed from the threaded hole, to allow the ring to be removed therefrom.

2. The orthodontic pin arrangement as claimed as claim 1, wherein said fastening member is a slotted head screw and can be tightened or loosened relative to said pin body with a corresponding slotted screwdriver.

3. The orthodontic pin arrangement as claimed as claim 1, wherein said fastening member is a Philip head screw and can be tightened or loosened relative to said pin body with a corresponding Philips screwdriver.

4. The orthodontic pin arrangement as claimed as claim 1, wherein said fastening member is a hexagonal head screw and can be tightened or loosened relative to said pin body with a corresponding hexagonal wrench.

5. The orthodontic pin arrangement as claimed as claim 1, wherein said elastic element is a tension spring having the ring and another ring provided at each end thereof.

6. The orthodontic pin arrangement as claimed as claim 1, wherein said elastic element is a tension spring having the ring and a hook separately provided at two ends thereof.

* * * * *